US011130148B2

(12) United States Patent
Hashimoto et al.

(10) Patent No.: US 11,130,148 B2
(45) Date of Patent: Sep. 28, 2021

(54) SYSTEM FOR MANUFACTURING MICRONEEDLE PREPARATION, AND AIR-CONDITIONING METHOD

(71) Applicant: HISAMITSU PHARMACEUTICAL CO., INC., Tosu (JP)

(72) Inventors: Eiji Hashimoto, Tsukuba (JP); Toshiyuki Matsudo, Tsukuba (JP); Shinpei Nishimura, Tsukuba (JP); Seiji Tokumoto, Tsukuba (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 808 days.

(21) Appl. No.: 14/894,397

(22) PCT Filed: May 29, 2014

(86) PCT No.: PCT/JP2014/064331
§ 371 (c)(1),
(2) Date: Nov. 27, 2015

(87) PCT Pub. No.: WO2014/192890
PCT Pub. Date: Dec. 4, 2014

(65) Prior Publication Data

US 2016/0107189 A1 Apr. 21, 2016

(30) Foreign Application Priority Data

May 29, 2013 (JP) ............................ JP2013-113449

(51) Int. Cl.
*B05C 15/00* (2006.01)
*F24F 3/16* (2021.01)
(Continued)

(52) U.S. Cl.
CPC ......... *B05C 15/00* (2013.01); *A61M 37/0015* (2013.01); *B05C 3/00* (2013.01);
(Continued)

(58) Field of Classification Search
CPC ......... F24F 3/14; F24F 3/16; B81B 2201/055; A61M 37/0015; A61M 2037/0053; B05B 7/1454
See application file for complete search history.

(56) References Cited

U.S. PATENT DOCUMENTS 4,848,673 A * 7/1989 Masuda ..................... B01J 2/16 241/5
5,000,624 A * 3/1991 Steiger .................. B05B 7/1404 406/124
(Continued)

FOREIGN PATENT DOCUMENTS

CN 201438016 U 4/2010
EP 1839764 A1 10/2007
(Continued)

OTHER PUBLICATIONS

European Search Report dated Apr. 25, 2017 issued in corresponding European Patent Application No. 14804072.8.
(Continued)

*Primary Examiner* — Jianying C Atkisson
*Assistant Examiner* — Meraj A Shaikh
(74) *Attorney, Agent, or Firm* — Nath, Goldberg & Meyer; Joshua B. Goldberg

(57) ABSTRACT

The present invention provides a system for manufacturing a therapeutic microneedle configured to regulate an air environment within a coating chamber for manufacturing a therapeutic microneedle by coating a microneedle with a coating liquid containing a drug, the system for manufacturing a therapeutic microneedle comprising an air compressor, a humidity regulator configured to regulate humidity of air supplied from the air compressor, and an air filter configured to eliminate microorganisms from air to be supplied to the inside of the coating chamber.

11 Claims, 13 Drawing Sheets

(51) Int. Cl.

| | |
|---|---|
| ***F24F 3/14*** | (2006.01) |
| ***B05C 21/00*** | (2006.01) |
| ***B05C 3/00*** | (2006.01) |
| ***B81C 99/00*** | (2010.01) |
| ***A61M 37/00*** | (2006.01) |
| ***F24F 8/10*** | (2021.01) |
| *B05D 3/04* | (2006.01) |

(52) U.S. Cl.

CPC .......... *B05C 21/00* (2013.01); *B81C 99/0025* (2013.01); *F24F 3/14* (2013.01); *F24F 8/10* (2021.01); *A61M 2037/0053* (2013.01); *B05D 3/0486* (2013.01); *B81B 2201/055* (2013.01)

(56) References Cited

U.S. PATENT DOCUMENTS

| | | | | |
|---|---|---|---|---|
| 5,766,671 | A | 6/1998 | Matsui | |
| 6,695,989 | B1 * | 2/2004 | Tsujimoto ................ | B01D 1/18 264/7 |
| 9,364,426 | B2 * | 6/2016 | Gill ................... | A61M 37/0015 |
| 2007/0023536 | A1 | 2/2007 | Baston | |
| 2008/0206546 | A1 | 8/2008 | Waki | |
| 2010/0280457 | A1 * | 11/2010 | Tokumoto ............ | A61K 9/0021 604/173 |
| 2010/0293807 | A1 * | 11/2010 | Bar-El .................... | F26B 21/14 34/282 |
| 2013/0072874 | A1 | 3/2013 | Tokumoto et al. | |
| 2013/0149471 | A1 * | 6/2013 | Kim ........................ | B05B 14/48 427/600 |

FOREIGN PATENT DOCUMENTS

| | | | | | |
|---|---|---|---|---|---|
| EP | 2051068 | A2 | | 4/2009 | |
| GB | 1296156 | | | 11/1972 | |
| GB | 1296156 | A | * | 11/1972 | ................ F24F 3/14 |
| JP | 2001202977 | A | | 7/2001 | |
| JP | 2002298883 | A | | 10/2002 | |
| JP | 2005249256 | A | | 9/2005 | |
| JP | 2006130596 | A | | 5/2006 | |
| JP | 2011500259 | A | | 1/2011 | |
| JP | 2011-206178 | A | | 10/2011 | |
| JP | 2013-48908 | A | | 3/2013 | |
| TW | 441826 | U1 | | 11/2012 | |
| WO | 2006/138287 | A2 | | 12/2006 | |
| WO | 2008139648 | A1 | | 11/2008 | |
| WO | 2009057112 | A2 | | 5/2009 | |
| WO | 2011148994 | A1 | | 12/2011 | |
| WO | 2014192887 | A1 | | 12/2014 | |

OTHER PUBLICATIONS

Office Action dated Nov. 14, 2017 in corresponding the TW counterpart Patent Application No. 103118823.

Official letter for International Search Report dated Sep. 9, 2014 corresponding to International application No. PCT/JP2014/064331.

"Filtration and Air-Cleaning Systems to Protect Building Environments from Airborne Chemical, Biological, or Radiological Attacks Department of Health and Human Services Centers for Disease Control and Prevention National Institute for Occupational Safety and Health; DHHS (NIOSH) Publication No. 2", pp. i-62, Apr. 30, 2003, XP055562628.

European Office Action dated Mar. 13, 2019 corresponding to application No. 14804072.8-1132.

* cited by examiner 200
10
12
30
24
22
28
14
16
20
18
21
26
L (a)

(b)

(c)

(a)

(b)

(a)

(b)

(a)

(b)

(a)

(b)

SYSTEM FOR MANUFACTURING MICRONEEDLE PREPARATION, AND AIR-CONDITIONING METHOD

This is a National Phase Application filed under 35 U.S.C. 371 as a national stage of PCT/JP2014/064331, filed May 29, 2014, an application claiming the benefit from the Japanese patent Application No. 2013-113449, filed May 29, 2013, the content of each of which is hereby incorporated by reference in its entirety.

TECHNICAL FIELD

The present invention relates to a system for manufacturing a therapeutic microneedle by coating microneedles with a drug and a method of air conditioning.

BACKGROUND ART

A therapeutic microneedle is known as a device for enhancing transdermal drug absorption. There is a method called dipping as a method for coating microneedles of a therapeutic microneedle with a drug (Patent Literature 1, for example). This is a method that fills a plurality of apertures formed in a mask plate with a coating liquid containing a drug and inserts microneedles into the apertures to coat the microneedles with the coating liquid. With this method, the microneedles can be coated with the coating liquid in a constant amount.

CITATION LIST

Patent Literature

Patent Literature 1: WO2008/139648

SUMMARY OF INVENTION

Technical Problem

However, when water is used as a solvent in the coating liquid, even when coating is performed using the method disclosed in Patent Literature 1, examination of a drug amount on the microneedles of the therapeutic microneedle obtained through a drying step after coating the microneedles with the coating liquid revealed that the drug amount varies depending on the date of manufacture, the time of manufacture, or other conditions and that stable manufacturing is difficult.

Given these circumstances, a main object of the present invention is to provide a system for manufacturing a therapeutic microneedle and a method of air conditioning that can prevent variations in a drug amount coating the microneedles.

Solution to Problem

First, the inventors of the present invention focused on an environment within a coating chamber in which drug coating of the microneedles is performed and have found out that property changes of the coating liquid are suppressed by keeping the inside of the coating chamber at certain ranges of temperature and humidity, whereby variations in the drug amount coating the microneedles can be suppressed.

However, it was difficult to directly control the temperature and humidity within the coating chamber by providing a temperature regulator and a humidity regulator inside the coating chamber. Given this situation, the inventors of the present invention have thought of means for maintaining the inside of the coating chamber at a desired temperature and humidity by supplying air regulated to be certain ranges of temperature and humidity in advance outside the coating chamber to the inside of the coating chamber.

When the property changes of the coating liquid are attempted to be suppressed by regulating the temperature and humidity within the coating chamber as described above, high humidity is required depending on the composition of the coating liquid. Meanwhile, the therapeutic microneedle is required to be manufactured in an aseptic state. In order to make a space an aseptic state, means for suppressing the propagation of microorganisms by reducing humidity is normally employed, and it has been conventionally considered difficult to simultaneously achieve two contradictory states, that is, the high humidity and the aseptic state in the system for manufacturing a therapeutic microneedle.

However, the inventors of the present invention have found out that even the contradictory requests can satisfactorily be fulfilled by employing means for supplying air regulated at certain ranges of temperature and humidity in advance outside the coating chamber to the coating chamber.

Specifically, the present invention provides a system for manufacturing a therapeutic microneedle that regulates an air environment within a coating chamber for manufacturing a therapeutic microneedle by coating a microneedle with a coating liquid containing a drug, the system for manufacturing a therapeutic microneedle comprising an air compressor, a humidity regulator configured to regulate humidity of air supplied from the air compressor, and an air filter configured to eliminate microorganisms from air to be supplied to an inside of the coating chamber.

By using the system for manufacturing a therapeutic microneedle having such a configuration in an environment at a temperature within a certain range, aseptic air with certain ranges of temperature and humidity can stably be supplied to the inside of the coating chamber.

The system for manufacturing a therapeutic microneedle may include a compressed air temperature regulator configured to regulate temperature of the air supplied from the air compressor. When temperature of an environment in which the system is placed changes, and the air supplied to the inside of the system by the air compressor is not a temperature within a desired range, if the system includes the compressed air temperature regulator, the air to be fed to the inside of the coating chamber can be regulated to any temperature, and humidity control can be performed more precisely.

It is preferable that the system for manufacturing a therapeutic microneedle include a humidity sensor and first control means for controlling the compressed air temperature regulator based on a signal corresponding to a humidity detected by the humidity sensor. Furthermore, the system for manufacturing a therapeutic microneedle may include a temperature sensor and second control means for controlling the compressed air temperature regulator based on a signal corresponding to a temperature detected by the temperature sensor. By thus providing the first control means and/or the second control means, the compressed air temperature regulator can be operated at any time in accordance with temperature and humidity within the coating chamber, whereby the temperature and humidity within the coating chamber can be controlled more efficiently and surely.

The humidity regulator that may be a water-vapor permeable membrane type humidity regulator in which the air supplied from the air compressor and water as a humidity regulation source are separated from each other by a water-vapor permeable membrane and that may be configured to regulate humidity by regulating temperature of the water can be used. The humidity regulator has such a configuration, whereby moisture can easily be supplied as water-vapor to the inside of the system, and precise humidity regulation can efficiently be performed. By supplying the water-vapor to the inside of the system through the water-vapor permeable membrane, even when microorganisms or the like are contained in the water, they can be prevented from being mixed into air flowing through the inside of the system for manufacturing a therapeutic microneedle.

It is preferable that the water-vapor permeable membrane be formed into a hollow fiber shape. The water-vapor permeable membrane has such a shape, whereby control of the temperature and humidity of the air to be supplied to the inside of the coating chamber can be performed efficiently and more precisely.

It is preferable that the humidity regulator include a water supplier configured to supply water. The humidity regulator has such a configuration, whereby water-vapor for regulating the humidity within the system can easily be supplied.

It is preferable that the water supplier comprises a constant-temperature water tank. By using the constant-temperature water tank for the water supplier, the water in the water supplier can easily be maintained at a constant temperature, whereby the temperature and humidity control can be performed more precisely.

The water supplier capable of regulating water temperature, that is, regulating the water temperature to any temperature within a temperature range is preferable. The water supplier has such a function, whereby the water in the water supplier can be maintained at any constant temperature within a wide range.

The system for manufacturing a therapeutic microneedle may include a humidity sensor and third control means for controlling water temperature of the water supplier based on a signal corresponding to a humidity detected by the humidity sensor. Furthermore, the system for manufacturing a therapeutic microneedle may include a temperature sensor and fourth control means for controlling the water temperature of the water supplier based on a signal corresponding to a temperature detected by the temperature sensor. By thus providing the third control means and/or the fourth control means, the water temperature of the water supplier can be operated at any time in accordance with the temperature and humidity within the coating chamber, whereby the temperature and humidity within the coating chamber can be controlled more efficiently and surely.

According to another embodiment of the present invention, provided is a method of air conditioning for regulating an air environment within a coating chamber for manufacturing a therapeutic microneedle by coating a microneedle with a coating liquid containing a drug, the method of air conditioning including a step of regulating humidity of air to be fed to the coating chamber by a humidity regulator, a step of eliminating microorganisms from the air by an air filter, and a step of introducing humidity-regulated, microorganism-eliminated air into the coating chamber.

According to such a method of air conditioning, by supplying air the temperature of which is within a certain range to the humidity regulator, aseptic air the temperature and humidity of which are within certain ranges can stably be supplied to the inside of the coating chamber.

Advantageous Effects of Invention

By the system for manufacturing a therapeutic microneedle or the method of air conditioning of the present invention, air the temperature and humidity of which are within certain ranges and that is in an aseptic state can stably be supplied to the inside of the coating chamber. With this, without being influenced by inter-day and intra-day fluctuations in temperature and humidity inside and outside the coating chamber, the inside of the coating chamber can be maintained at certain ranges of temperature and humidity, whereby fluctuations in coating liquid properties within the coating chamber can be suppressed. Consequently, when microneedles is coated with a coating liquid containing a drug in an air environment regulated by the system for manufacturing a therapeutic microneedle or the method of air conditioning of the present invention, a therapeutic microneedle to which a constant drug amount is coated can stably be manufactured.

DESCRIPTION OF EMBODIMENTS

Figure 1:
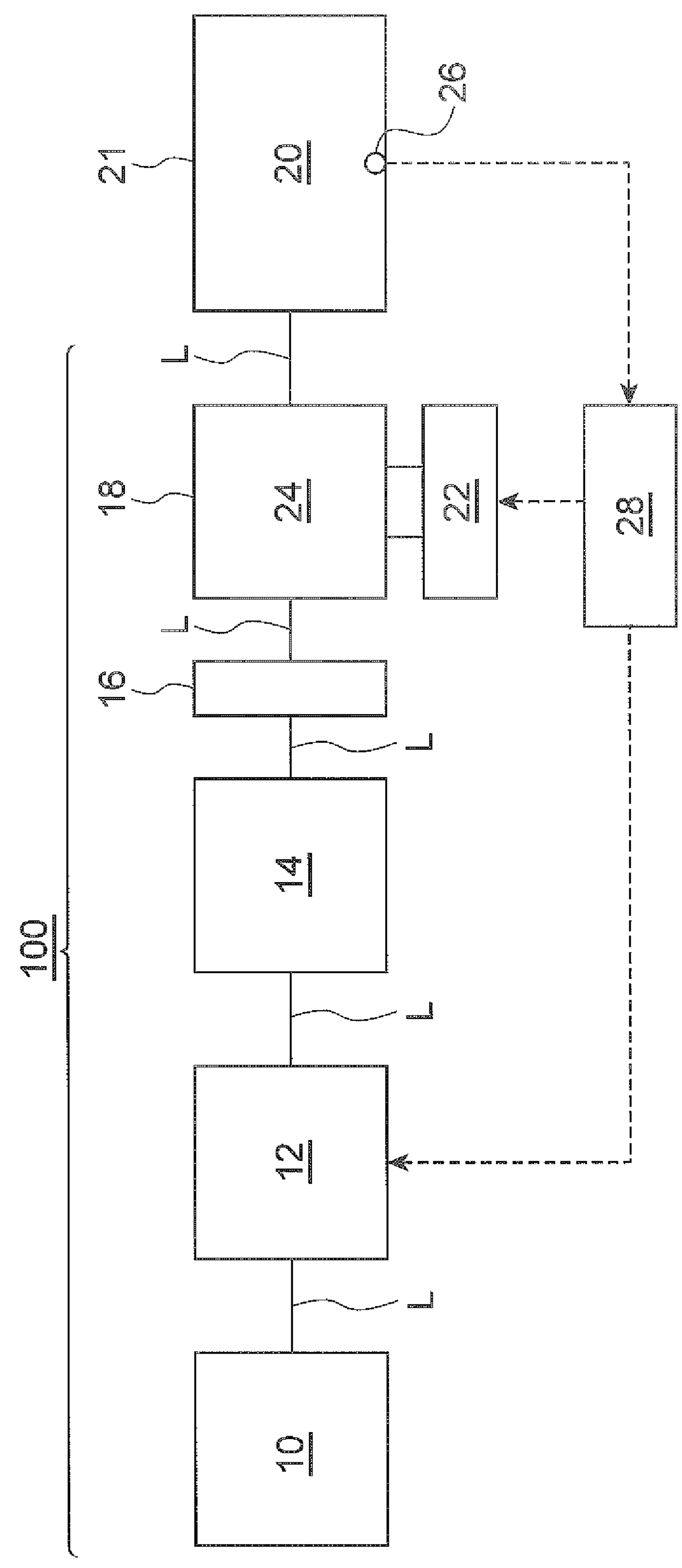
FIG. 1 is a block configuration diagram illustrating an embodiment of a system for manufacturing a therapeutic microneedle.

Preferred embodiments of a system for manufacturing a therapeutic microneedle and a method of air conditioning according to the present invention will be described below with reference to the drawings. The same or corresponding parts in the drawings will be attached with the same symbols, and detailed descriptions thereof will be omitted.

The system for manufacturing a therapeutic microneedle (hereinafter also simply referred to as a "system" in some cases) according to the present embodiment creates an air environment suitable for performing working for coating microneedles with a coating liquid containing a drug to manufacture a therapeutic microneedle. In the present specification, humidity refers to relative humidity.

FIG. 1 is a block configuration diagram illustrating a first embodiment of a system for manufacturing a therapeutic microneedle of the present invention. In the first embodiment, a system 100 for manufacturing a therapeutic microneedle is configured by an air compressor 10, a compressed air temperature regulator 12, an airflow rate regulator 14, an air filter 16, and a humidity regulator 18 being connected with each other in this order via an air blowing line L. A terminal of the air blowing line L is connected to a coating chamber 20 in which microneedles are arranged and coating of a drug is performed.

Next, each component of the system 100 for manufacturing a therapeutic microneedle according to the present embodiment will be described.

The air compressor 10 in the system 100 for manufacturing a therapeutic microneedle according to the present embodiment may be any one that can generate an airflow with a desired air velocity (flow rate), and a compression ratio of the air compressor 10 is not particularly limited. Consequently, for example, not limited to air compressors stipulated in JIS (B 0132: 2005), an air blower with a low compression ratio can also be used as the air compressor 10. It is preferable that an airflow rate of air supplied to the inside of the present system 100 by the air compressor 10 be 10 to 250 L/min, and it is more preferable that the airflow rate be 20 to 100 L/min. The airflow rate may be 10 L/min or less and may be 0.3 to 10 L/min, for example. The airflow rate of the supplied air can be calculated as an airflow rate per a volume of the coating chamber 20. It is preferable that the airflow rate of the air supplied per a volume of 1 L of the coating chamber 20 be 28 to 696 L/min, and it is more preferable that the airflow rate be 56 to 278 L/min. The airflow rate of the air supplied per a volume of 1 L of the coating chamber 20 may be 28 L or less and may be 1 to 28 L/min, for example. As the air supplied to the inside of the present system 100 by the air compressor 10, air present outside the system can be used, and any gas may be mixed therewith in accordance with a composition of the coating liquid to coat the microneedles.

Although the airflow rate (flow rate) of the air from the air compressor 10 can be regulated by a function of the air compressor 10 itself, it is preferable that the airflow rate of the air flowing through the inside of the present system 100 be able to be regulated more precisely by connecting the airflow rate regulator 14 to the downstream side of the air compressor 10. When the present system 100 includes the airflow rate regulator 14, by regulating the airflow rate of the air flowing through the inside of the present system 100, a drug amount coating the microneedles can also be regulated. When the airflow rate of the air flowing through the inside of the present system 100 is increased by the airflow rate regulator 14, for example, the drug amount coating the microneedles within the coating chamber 20 can be increased. In contrast, when the airflow rate is decreased by the airflow rate regulator 14, the drug amount coating the microneedles can be decreased. When the airflow rate is a certain amount or more, for example, 2.0 L/min or more, temperature and humidity distribution within the coating chamber can be made more uniform.

The compressed air temperature regulator 12 in the system 100 for manufacturing a therapeutic microneedle according to the present embodiment can regulate the temperature of the air supplied from the outside to the inside of the present system 100 by the air compressor 10 to any temperature. Consequently, even when there are inter-day and intra-day fluctuations in temperature of an outside air of the present system 100, by providing the compressed air temperature regulator 12, the temperature of the air flowing through the inside of the present system 100 can be maintained within a desired range regardless of the outside environment. It is preferable that the compressed air temperature regulator 12 be able to adapt to a range of about 5 to 40° C. as the temperature of the air injected into the compressed air temperature regulator 12. Although the temperature of the air to be fed from the compressed air temperature regulator 12 to the air blowing line L on the downstream side can freely be set in accordance with the composition of the used coating liquid, it is preferable that the temperature of the air be set near room temperature, and it is more preferable that the temperature of the air be set to 20 to 30° C. from the viewpoint of the efficiency of temperature regulation. It is preferable that the compressed air temperature regulator 12 that can control temperature of discharged air with an accuracy of ±0.5° C. or less be used. As the compressed air temperature regulator 12, the one that can precisely control the temperature of the compressed air such as ones based on a temperature control system, a radiational cooling system or the like can be used.

The air filter 16 in the system 100 for manufacturing a therapeutic microneedle according to the present embodiment can be used without limitation so long as the air filter 16 can capture and eliminate microorganisms such as bacteria and Eumycetes contained in passing air. By using the air filter 16, not only microorganisms, but also dust in the air can be removed. It is preferable that a pore size of the air filter 16 be 0.2 μm or less from the viewpoint of microorganism-eliminating efficiency. Two or more air filters can be used, such as a combination of a filter having a dust removal effect such as a high efficiency particulate air (HEPA) filter and an air filter having a microorganism-eliminating effect, for example. Within the system 100 according to the present embodiment, the air supplied from the air compressor 10 constantly flows toward an aperture 21 of the coating chamber 20, and by providing the air filter 16 in the present system 100, the inside of the coating chamber 20 can be made aseptic more surely. Although being installed on the downstream side of the airflow rate regulator 14, the air filter 16 can be installed at any position on the air blowing line L on the downstream side of the air compressor 10 within the present system 100.

The humidity regulator 18 in the system 100 for manufacturing a therapeutic microneedle according to the present embodiment can regulate and maintain the air flowing through the inside of the present system 100 to and at a desired humidity by being used in combination with the above-described compressed air temperature regulator 12. The humidity of the air obtained by regulation by the present system 100 can be 70 to 95% (RH), for example, and can also be 95% (RH) or more. It is preferable that the humidity regulator 18 be of the water-vapor permeable membrane type having a water-vapor permeable membrane. As the humidity regulator 18 of the water-vapor permeable membrane type, the one including a water supplier 22 and a water-vapor permeable membrane device 24 having a membrane with water-vapor permeability (a water-vapor permeable membrane) can be used, for example. As the water-vapor permeable membrane, for example, an ion exchange resin formed into a hollow fiber shape can be used. The water-vapor permeable membrane has a characteristic of causing water-vapor to permeate therethrough and causing liquid water not to permeate therethrough.

For the water supplier 22, it is effective to use a constant-temperature water tank in order to control water temperature to be constant. Furthermore, the constant-temperature water tank that can be regulated within a temperature range and can be regulated to any temperature with high precision is preferable. It is preferable that water to be used in the water supplier 22 be pure water in order to ensure an aseptic state. Water supplied from the water supplier 22 to the water-vapor permeable membrane device 24 is vaporized through the water-vapor permeable membrane and is supplied as water-vapor to the inside of the present system 100.

Although various forms can be considered as the water-vapor permeable membrane device 24, it is preferable that a hollow fiber module, in which many water-vapor permeable membranes formed in a hollow fiber shape are fixed in a bundle shape, be used from the viewpoint of efficiency. When using the hollow fiber module, the hollow fiber module is connected to the air blowing line L of the present system 100 so that the air flowing through the inside of the present system 100 will pass through the inside of a hollow fiber shaped water-vapor permeable membrane. It is preferable that water the water temperature of which is controlled by the water supplier 22 or preferably the constant-temperature water tank be configured to flow so as to be in contact with the outside of the hollow fiber shaped water-vapor permeable membrane and to circulate between the hollow fiber shaped water-vapor permeable membrane and the water supplier 22 at all times. When water at a constant temperature and a gas at a certain range of temperature are brought into contact with each other through the hollow fiber shaped water-vapor permeable membrane, a gas at a certain range of humidity is derived from the hollow fiber module. Consequently, the air temperature-regulated by the compressed air temperature regulator 12 is introduced into the hollow fiber module, and the pure water at a constant temperature passes from the constant-temperature water tank through the hollow fiber module, whereby the air from the hollow fiber module flows downstream while having a desired range of humidity. By controlling the water temperature of the water supplier 22 such as the constant-temperature water tank, humidity control can also be performed with high precision. In other words, by increasing the water temperature up to a certain temperature, the air flowing through the inside of the present system 100 can be humidified to a humidity corresponding to that temperature, and in contrast, by decreasing the water temperature to a certain temperature, the air flowing through the inside of the present system 100 can be dehumidified to a humidity corresponding to that temperature. When using the water-vapor permeable membrane device 24 having the hollow fiber module, the hollow fiber module has filter function, whereby microorganisms that may be contained in the water within the water supplier 22 are captured by the hollow fiber module and can be prevented from being mixed into the air flowing through the inside of the present system 100.

The air blowing line L in the system 100 for manufacturing a therapeutic microneedle according to the present embodiment in any form can be used so long as the air blowing line L involves no air leak and intrusion regardless of its material. In order to further ensure the effect of temperature regulation by the compressed air temperature regulator 12 and maintain the air environment within the coating chamber 20 at a desired temperature more stably, it is preferable that the air blowing line L have an adiabatic effect. As a method for causing the air blowing line L to have the adiabatic effect, providing a heat insulating material so as to cover the circumference of the air blowing line L may be acceptable, or changing the material of the air blowing line L itself to a material having the adiabatic effect may be acceptable.

The air temperature and humidity of which are within certain ranges derived from the humidity regulator 18 is fed to the coating chamber 20 for manufacturing a therapeutic microneedle by coating the microneedles with the coating liquid containing the drug therewithin. The coating chamber 20 has an aperture 21 in part of its wall face. This aperture 21 has a role not only as a discharge port through which the air supplied from the present system 100 is discharged but also as an inlet for the therapeutic microneedle to which the coating liquid is coated. When the coating chamber 20 is box-shaped, for example, the aperture 21 may be provided in an upper face of the coating chamber 20 or may be provided in a side face or a lower face. In order to sufficiently fill the inside of the coating chamber 20 with a desired air environment, it is preferable that the aperture 21 and a connecting part with the present system 100 be sufficiently separated from each other. It is preferable that the airflow rate of the air blown into the coating chamber 20 be maintained at a sufficiently high level. By maintaining this airflow rate at a sufficiently high level, the inside of the coating chamber 20 is maintained at positive pressure with respect to the outside of the present system 200, and outside air can be prevented from flowing into the inside of the coating chamber 20 from the aperture 21. Consequently, the inside of the coating chamber 20 can be maintained at a desired temperature and humidity, and microorganisms can be prevented from entering the inside of the coating chamber 20 from the aperture 21.

It is preferable that a temperature and humidity sensor (a temperature sensor and a humidity sensor) 26 be installed inside the coating chamber 20 in order to grasp temperature and humidity of air within the coating chamber 20. This is because by enabling whether the air supplied to the inside of the coating chamber 20 by the present system 100 is maintained at the desired temperature and humidity to be grasped at any time, the compressed air temperature regulator 12 and the humidity regulator 18 are operated one by one in accordance with the temperature and humidity within the coating chamber 20, whereby the temperature and humidity of the air within the coating chamber 20 can be controlled further strictly. A system, or a feedback system may be provided that sends signals corresponding to the temperature and humidity within the coating chamber 20 detected by the temperature and humidity sensor 26 to a controller (first control means and/or second control means for controlling the compressed air temperature regulator 12 as well as third control means and/or fourth control means for controlling the water temperature of the water supplier 22) 28 and based on the signals causes the controller 28 to operate the compressed air temperature regulator 12 or the water supplier 22 within the humidity regulator 18. Specifically, the feedback system can be provided that operates a heating mechanism of the water supplier 22 when detecting a humidity decrease within the coating chamber 20 and operates a cooling mechanism of the water supplier 22 when, in contrast, detecting a humidity increase within the coating chamber 20, for example. The feedback system can be provided that accelerates the heating of the heating mechanism of the compressed air temperature regulator 12 or suppresses the cooling of the cooling mechanism when it is detected that the temperature within the coating chamber 20 is lower than a certain lower limit and suppresses the heating of the heating mechanism of the compressed air temperature regulator 12 or accelerates the cooling of the cooling mechanism when, in contrast, it is detected that the temperature within the coating chamber 20 is higher than a certain higher limit, for example. By providing such a feedback system, the temperature and humidity control within the coating chamber 20 can be performed more efficiently and surely.

When the system 100 for manufacturing a therapeutic microneedle of the above configuration is operated, first, air is taken in from the outside by the air compressor 10 and is supplied to the inside of the present system 100. The air taken in by the air compressor 10 passes through the air blowing line L, is injected into the compressed air temperature regulator 12, and is regulated to a certain temperature. The air regulated to the certain temperature by the compressed air temperature regulator 12 passes through the air blowing line L, is subjected to airflow rate regulation as needed, and is subjected to microorganism-elimination by the air filter 16. The air microorganism-eliminated by the air filter 16 is injected into the humidity regulator 18 and is regulated to a certain humidity. The aseptic air the temperature and humidity of which have thus been regulated passes through the air blowing line L and is supplied to the inside of the coating chamber 20. Air present within the coating chamber 20 until that time is discharged from the aperture 21 provided in the part of the wall face constituting the coating chamber 20, and the inside of the coating chamber 20 is filled with the aseptic air having the desired temperature and humidity. From the aperture 21, the air supplied to the inside of the coating chamber 20 by the present system 100 is discharged at any time. The air flowing through the inside of the present system 100 flows unidirectionally toward the aperture 21 constantly with a certain air velocity by the air blowing power of the air compressor 10. Consequently, the air does not stagnate within the present system 100, and even when microorganisms are present within the present system 100, their propagation is suppressed.

Within the coating chamber 20, the coating liquid containing the drug are prepared in advance. While coating work is performed, as described above, the inside of the coating chamber 20 is constantly in the environment with the certain ranges of temperature and humidity and the aseptic state, whereby a vaporization reaction of water contained in the coating liquid and a liquefaction reaction of water-vapor in the air are controlled, and changes in the properties of the coating liquid are suppressed. With this, variations in the drug amount coating the microneedles can be suppressed, and the therapeutic microneedle can be stably produced in the aseptic environment. It is preferable that a variation coefficient (CV) value indicating the degree of the variations in the drug amount coating the microneedles be 10% or less, and it is further preferable that the CV value be 5% or less. The CV value is a value in which a standard deviation is divided by an average and is expressed as a percentage.

Figure 2:
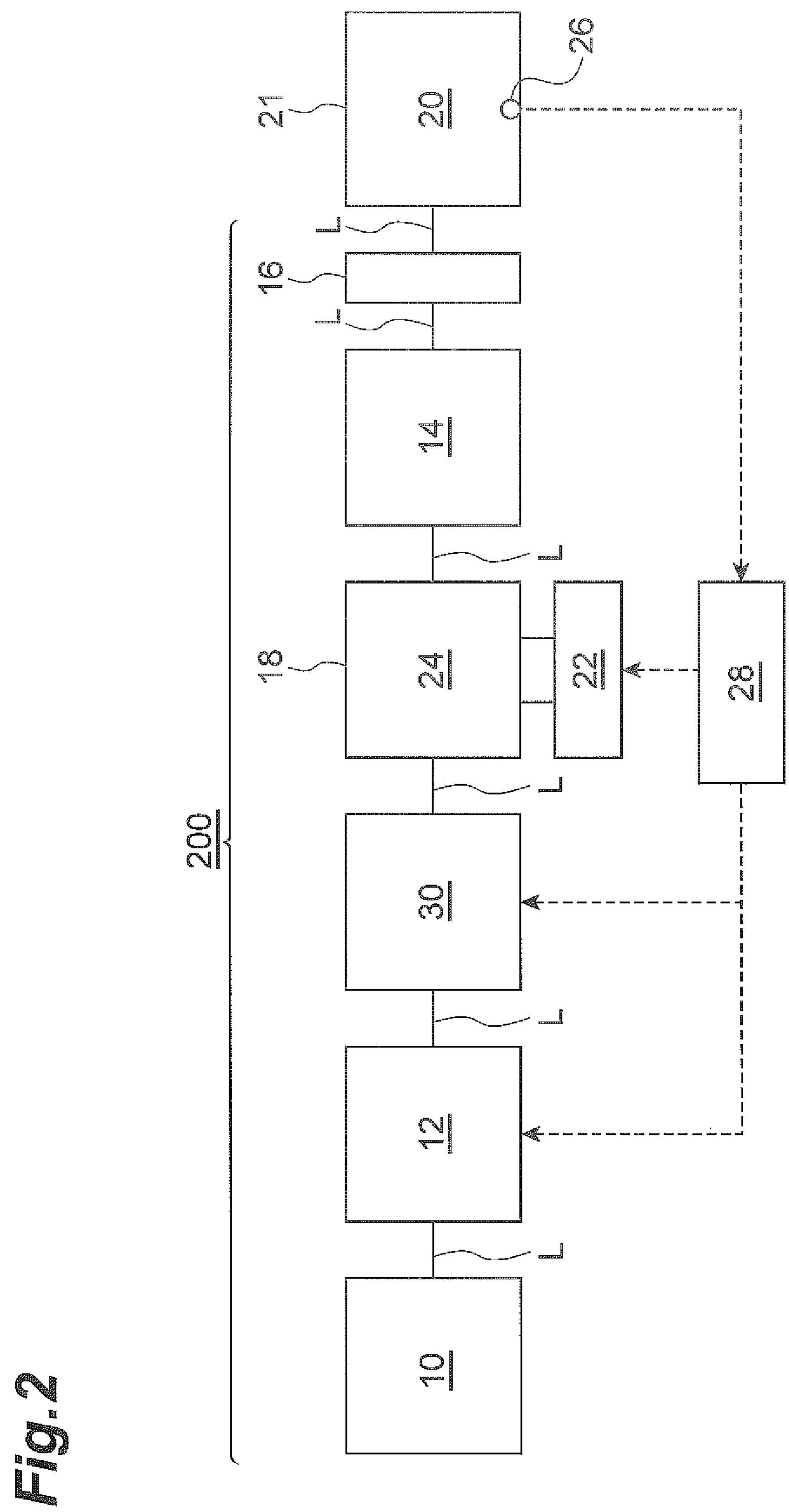
FIG. 2 is a block configuration diagram illustrating an embodiment of the system for manufacturing a therapeutic microneedle.

FIG. 2 is a block configuration diagram illustrating a second embodiment of a system 200 for manufacturing a therapeutic microneedle according to the present invention. The system of the second embodiment has a characteristic point different from the system 100 of the first embodiment in that a pressure regulator 30 is connected to the downstream of the compressed air temperature regulator 12 and the upstream of the humidity regulator 18. This configuration is made in consideration of the point that, in a system using the water-vapor permeable membrane device 24 having the water-vapor permeable membrane, especially the water-vapor permeable membrane device 24 of the hollow fiber module type, the water-vapor permeable membrane device 24 can regulate the humidity of the air to be derived by also the pressure of the introduced air. In other words, by also controlling the pressure of the air to be injected into the humidity regulator 18 by the pressure regulator 30, the humidity of the air to be supplied to the inside of the coating chamber 20 can precisely be controlled.

When using the pressure regulator 30, it is preferable that the airflow rate regulator 14 and the air filter 16 be provided downstream of the humidity regulator 18 by reason of installation layout. A line that bypasses the pressure regulator 30 so as to enable air to be directly conveyed to the humidity regulator 18 from the compressed air temperature regulator 12 may be provided. Furthermore, concerning also this system 200 according to the second embodiment, as illustrated in the drawing, it is preferable that the feedback system be provided, the signals corresponding to the temperature and humidity within the coating chamber 20 be sent to the controller 28 by the temperature and humidity sensor 26, and the controller 28 be able to operate the water supplier 22 within the humidity regulator 18, the compressed air temperature regulator 12, and the pressure regulator 30 in accordance with the signals.

Although the above embodiment was described in which the temperature of the environment in which the present system 100 is placed fluctuates, the compressed air temperature regulator 12 is not necessarily provided in the configuration when the air supplied from the air compressor 10 is already maintained at the certain range of temperature in such a case as when the present system 100 is used in a space in which the temperature of the entire environment is controlled.

Although the humidity regulator 18 was described as having the water-vapor permeable membrane device 24 having the hollow fiber shaped water-vapor permeable membrane, the water-vapor permeable membrane is not limited to the hollow fiber shape, and one of any shape can be used. The humidity regulator 18 illustrated in FIG. 3 includes a water-vapor permeable membrane 23 provided in a partition type. The water-vapor permeable membrane 23 in FIG. 3 separates the air supplied from the air compressor 10 to the inside of present system 200 and water as a humidity regulation source from each other. The moisture is supplied to the air flowing through a flow passage of the present system 100 as water-vapor through the water-vapor permeable membrane 23.

Figure 3:
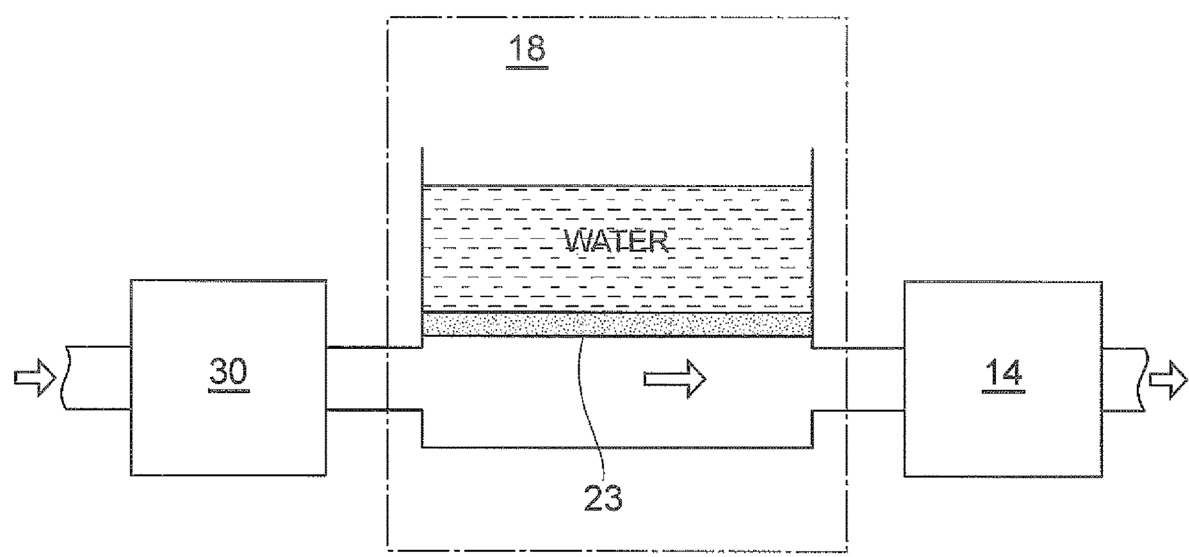
FIG. 3 is a sectional view schematically illustrating an embodiment of a humidity regulator in the system for manufacturing a therapeutic microneedle.

The pressure regulator 30 in FIG. 3 is connected to the outside on the upstream side of the humidity regulator 18 and regulates the pressure of the air to be introduced into the inside of the humidity regulator 18. The pressure regulator 30 may be configured so as to be provided within the humidity regulator 18 and regulate the pressure of the air introduced into the inside of the humidity regulator 18.

Figure 4:
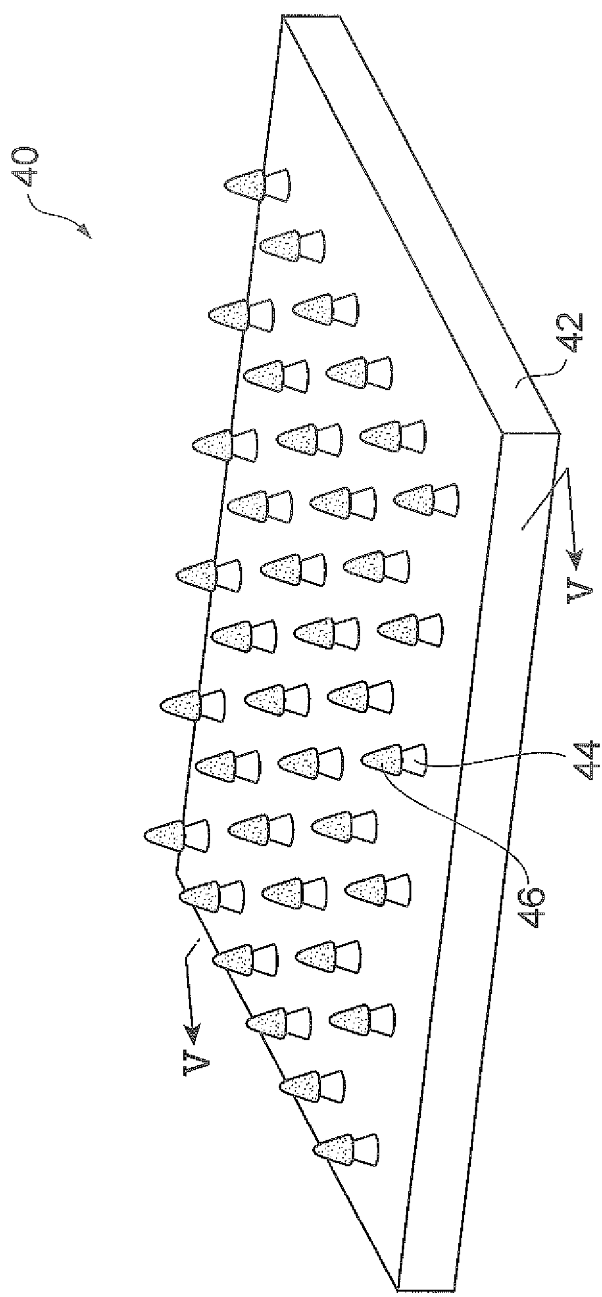
FIG. 4 is a perspective view illustrating an example of a therapeutic microneedle.

A summary of a method for manufacturing a therapeutic microneedle using the system for manufacturing a therapeutic microneedle in the above configuration will be described. FIG. 4 is a perspective view illustrating an example of a therapeutic microneedle manufactured using the system according to the present embodiment. A therapeutic microneedle 40 illustrated in FIG. 4 includes a substrate 42, a plurality of microneedles 44 arranged on the substrate 42 in a two-dimensional manner, and a coating layer 46 formed on the microneedles 44. The coating layer 46 is coated with the system for manufacturing a therapeutic microneedle according to the present embodiment, and it is preferable that at least part of its volatile component be removed.

The substrate 42 is a base for supporting the microneedles 44. It is preferable that an area of the substrate 42 be 0.5 to 10 cm$^2$, and it is further preferably 1 to 5 cm$^2$ and more preferably 1 to 3 cm$^2$. A substrate of a desired size may be configured by connecting a plurality of substrates 42 with each other.

Each of the microneedles 44 is a microscopic structure, and its height (length) is preferably 50 to 600 By setting the length of the microneedle 44 to 50 μm or more, administration of the drug contained in the coating liquid can surely be performed. By setting the length of the microneedle 44 to 600 μm or less, the microneedle avoids contacting with nerves, whereby the possibility of pain is surely reduced, and the possibility of bleeding can surely be avoided. If the length of the microneedle 44 is 500 μm or less, the drug in an amount that should be intradermally injected can efficiently be administered, and administration without piercing a basal membrane is also made possible. It is particularly preferable that the length of the microneedle 44 be 300 to 500 μm.

The microneedle 44 means a convex structure, the structure in a needle shape or the structure including a needle shape in a broad means. However, the microneedle is not limited to one of the needle shape having an acute tip and may be one of a shape the tip of which is not acute. When the microneedle 44 is a conical structure, it is preferable that a diameter in its base be about 50 to 200 μm. Although the microneedle 44 in the present embodiment is conical-shaped, the microneedle 44 may be a microneedle of a polygonal pyramidal shape such as a quadrangular pyramidal shape or another shape.

The microneedles 44 are typically provided spaced apart from each other so that their density will be 1 to 10 per 1 millimeter (mm) for a row of the needles. In general, adjacent rows are separated from each other by substantially an equal distance with respect to a space of the needles within the rows and have a needle density of 100 to 10,000 per 1 cm$^2$. If there is a needle density of 100 or more, skin can efficiently be pierced. In contrast, a needle density exceeding 10,000 makes it difficult to maintain strength of the microneedles 44. A density of the microneedles 44 is preferably 200 to 5,000, further preferably 300 to 2,000, and particularly preferably 400 to 850.

Although examples of a material of the substrate 42 or the microneedles 44 include silicone, silicon dioxide, ceramics, metals (stainless, titanium, nickel, molybdenum, chromium, cobalt, and the like), and synthetic or natural resin materials, considering antigenicity of the microneedles and a unit price of the material, particularly preferable is a synthetic or natural resin material such as a biodegradable polymer such as polylactic acid, polyglycolide, polylactic acid-co-polyglycolide, pullulan, caprolactone, polyurethane, or a polyanhydride or polycarbonate, polymethyl methacrylate, ethylene vinyl acetate, polytetrafluoroethylene, polyoxymethylene, or the like as a non-degradable polymer. Also preferable is hyaluronic acid, sodium hyaluronate, pullulan, dextran, dextrin, chondroitin sulfate, or the like as a polysaccharide.

Examples of a method for manufacturing the substrate 42 or the microneedles 44 include wet etching processing or dry etching processing using a silicon substrate, precise machining (discharge processing, laser processing, dicing processing, hot emboss processing, injection molding processing, and the like) using metal or resin, and machining processing. By these methods of processing, the substrate 42 and the microneedles 44 are integrally formed. Examples of a method for making the microneedles 44 hollow include a method that manufactures the microneedles 44 and then performs secondary processing by a laser or other tools.

The therapeutic microneedle 40 includes the coating layer 46 on the microneedles 44, in which it is preferable that the coating layer 46 be formed by coating with or applying the coating liquid. Examples of a method of coating include spray coating and dip coating, and the dip coating is preferable. Although in FIG. 4 the coating layer 46 is formed on all microneedles 44, the coating layer 46 may be formed only on part of the plurality of microneedles 44. Although the coating layer 46 is formed only on the tips of the microneedles 44 in FIG. 4, the coating layer 46 may be formed so as to cover the entire microneedles 44. Furthermore, the coating layer 46 may be formed on the substrate 42.

Figure 5:
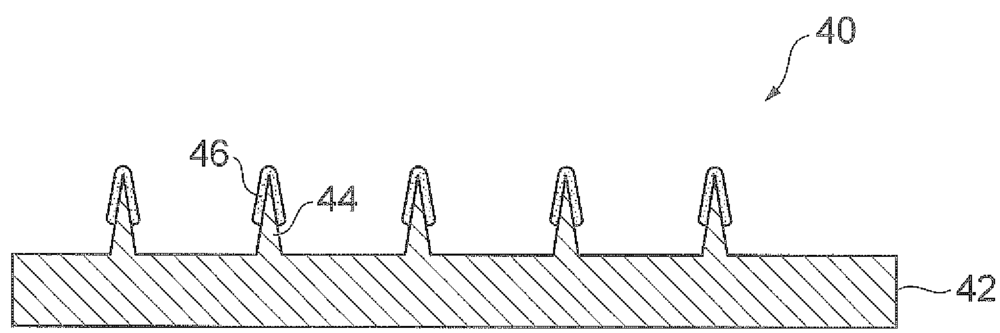
FIG. 5 is a V-V line sectional view of the therapeutic microneedle in FIG. 4.

FIG. 5 is a V-V line sectional view in FIG. 4. As illustrated in FIG. 5, the therapeutic microneedle 40 includes the substrate 42, the microneedles 44 provided on the substrate 42, and the coating layer 46 provided on the microneedles 44. The coating layer 46 adhering on the microneedles contains the drug and can be manufactured through the above processes, for example.

Figure 6:
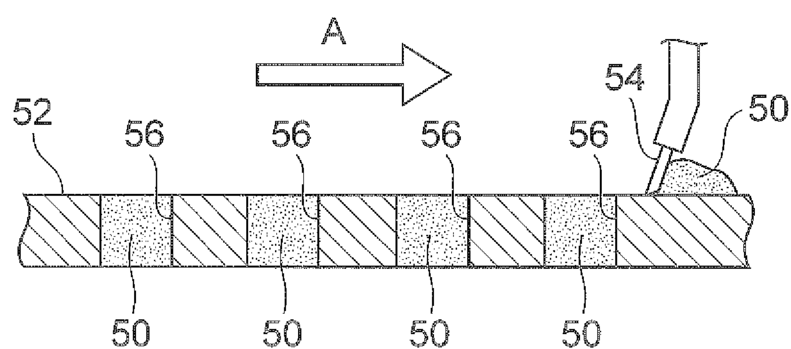
FIG. 6 (*a*) through (*c*) are diagrams illustrating an example of a method for manufacturing a therapeutic microneedle.
Figure 6:
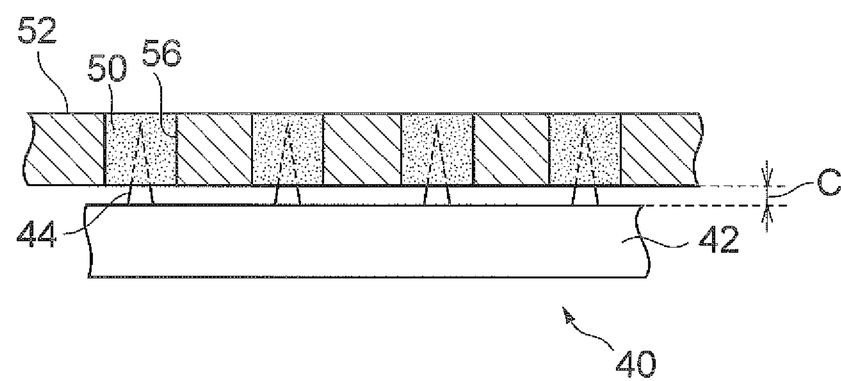
Figure 6:
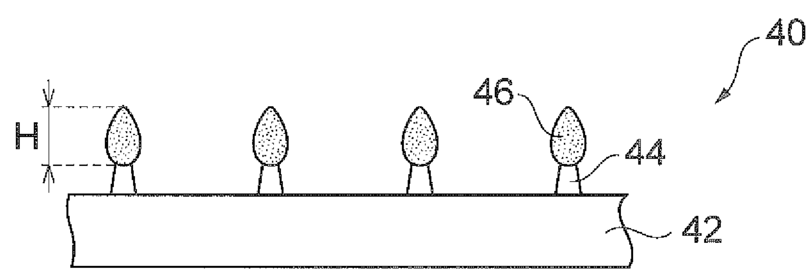

FIGS. 6 (*a*), (*b*), and (*c*) are diagrams illustrating an example of a method of manufacturing the therapeutic microneedle 40. This method is referred to as dipping. In this method, first, as illustrated in FIG. 6 (*a*), a coating liquid 50 is swept in an arrow A direction on a mask plate 52 with a spatula 54. With this, the coating liquid 50 is filled into apertures 56. Subsequently, as illustrated in FIG. 6 (*b*), the microneedles 44 are inserted into the apertures 56 of the mask plate 52. Thereafter, as illustrated in FIG. 6 (*c*), the microneedles 44 are pulled out of the apertures 56 of the mask plate 52. With this, the coating liquid 50 is made to adhere on the microneedles 44. The coating liquid 50 may be made to adhere on the substrate 42.

By performing the working illustrated in FIGS. 6 (*a*), (*b*), and (*c*) within the coating chamber, the therapeutic microneedle is manufactured; as a condition in that situation, the inside of the coating chamber is made an aseptic air environment the temperature and humidity of which are controlled by using the system according to the present embodiment. Specifically, the devices in the present system are started up, and the air supplied from the air compressor is regulated to a desired environment and is blown into the coating chamber. By feeding temperature and humidity measurement results within the coating chamber back to the constant-temperature water tank or other components, the air environment with the desired temperature and humidity is stably maintained. By performing coating in the thus obtained air environment, the microneedles can stably be coated with the coating liquid containing a constant drug content.

After performing the coating as described above, a volatile component of the coating liquid 50 on the microneedles 44 is removed by air drying, vacuum drying, or a combination thereof as a known method. With this, the coating layer 46 firmly adheres on the microneedles 44 and typically becomes glassy or solid, whereby the therapeutic microneedle 40 is manufactured. A water content of the coating layer 46 is normally 55% by mass or less based on the total amount of the coating layer 46, preferably 30% by mass or less, and further preferably 10% by mass or less. By the above method, dripping of the adhering coating liquid 50 is prevented. The dripping indicates dripping of the coating liquid from needle tips and means that in FIG. 6 (*c*) an H part lengthens.

A height H of the coating layer 46 adhering on the microneedles 44 is regulated by a clearance (gap) C illustrated in FIG. 6 (*b*). This clearance C is defined by the distance (a thickness of the substrate 42 is not involved) from a base of the microneedles 44 to a surface of the mask plate 52 and is set in accordance with tension of the mask plate 52 and the length of the microneedles 44. A range of the distance of the clearance C is preferably 0 to 500 μm. If the distance of the clearance C is zero, it means that the coating liquid 50 is coated to the entire microneedles 44. Although the height H of the coating liquid 50 adhering on the microneedles 44 varies by the height of the microneedles 44, the height H can be 0 to 500 pin, normally 10 to 500 μm, preferably about 30 to 300 μm, and particularly preferably about 40 to 250 μm. In order to effectively use the drug within the coating liquid 50, it is preferable that the drug be made to be present concentratedly in part of the microneedle, or on the tip of the needle, and from the viewpoint of stimulation to skin and a transfer rate of the drug to skin, it is preferable that the drug be made to be present within 200 μm of the tip. The coating liquid 50 can dissolve a polymer compound in an aqueous solution, for example, has high viscosity, and can thereby form the coating layer 46 in the part of the microneedle. When skin is punctured with the microneedles 44, the coating liquid 50 held on the microneedles 44 in such a form is simultaneously intradermally inserted.

It is preferable that a thickness of the coating layer 46 after being dried adhering on the microneedles 44 be less than 50 μm, and it is more preferably less than 40 μm and further preferably 1 to 30 μm. In general, the thickness of the coating layer 46 adhering on the microneedles is an average thickness measured across the surface of the microneedles 44 after being dried. The thickness of the coating layer 46 adhering on the microneedles 44 can be increased by applying a plurality of coatings of the coating liquid 50, in other words, repeating adherence processing after the coating liquid 50 is made to adhere.

The drug contained in the coating liquid 50 is considered to be, but are not limited to, a polymer compound such as a peptide, a protein, a DNA, or an RNA and may be a vaccine, a low molecular weight peptide, a saccharide, or a nucleic acid so long as its molecular weight is about 1,000. Examples of a physiologically active substance include naltrexone, cetrorelix acetate, taltirelin, nafarelin acetate, prostaglandin A1, alprostadil, α-interferon, β-interferon for multiple sclerosis, erythropoietin, follitropin β, follitropin α, G-CSF, GM-CSF, human chorionic gonadotropin, luteinizing hormone, salmon calcitonin, glucagon, GNRH antagonist, insulin, human growth hormone, filgrastim, heparin, low molecular weight heparin, somatropin, incretin, and GLP-1 derivatives. Examples of vaccines include a Japanese encephalitis vaccine, a rotavirus vaccine, an Alzheimer's disease vaccine, an arterial sclerosis vaccine, a cancer vaccine, a nicotine vaccine, a diphtheria vaccine, a tetanus vaccine, a pertussis vaccine, a Lyme disease vaccine, a rabies vaccine, a pneumococcal vaccine, a yellow fever vaccine, a cholera vaccine, a vaccinia vaccine, a tuberculosis vaccine, a rubella vaccine, a measles vaccine, a mumps vaccine, a botulinum vaccine, a herpes vaccine, other DNA vaccines, and a hepatitis B vaccine.

Other examples thereof include hypnotics/tranquilizers (flurazepam hydrochloride, rilmazafone hydrochloride, phenobarbital, amobarbital, and the like); antipyretic/antiphlogistic analgesics (butorphanol tartrate, perisoxal citrate, acetaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, and the like); steroidal anti-inflammatory agents (hydrocortisone, prednisolone, dexamethasone, betamethasone, and the like); analeptics/stimulants (methamphetamine hydrochloride, methylphenidate hydrochloride, and the like); psychotropic agents (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazodone, lofepramine, milnacipran, duloxetine, venlafaxine, chlorpromazine hydrochloride, thioridazine, diazepam, meprobamate, etizolam, and the like); hormone drugs (estradiol, estriol, progesterone, norethisterone acetate, metenolone acetate, testosterone, and the like); local anesthetics (lidocaine hydrochloride, procaine hydrochloride, tetracaine hydrochloride, dibucaine hydrochloride, propitocaine hydrochloride, and the like); urinary drugs (oxybutynin hydrochloride, tamsulosin hydrochloride, propiverine hydrochloride, and the like); skeletal muscle relaxants (tizanidine hydrochloride, eperisone hydrochloride, pridinol mesilate, suxamethonium hydrochloride, and the like); genital drugs (ritodrine hydrochloride and meluadrine tartrate); antiepileptic drugs (sodium valproate, clonazepam, carbamazepine, and the like); autonomic agents (carpronium chloride, neostigmine bromide, bethanechol chloride, and the like); anti-Parkinson's disease agents (pergolide mesilate, bromocriptine mesilate, trihexyphenidyl hydrochloride, amantadine hydrochloride, ropinirole hydrochloride, talipexole hydrochloride, cabergoline, droxidopa, biperiden, selegiline hydrochloride, and the like); diuretics (hydroflumethiazide, furosemide, and the like); respiratory accelerators (lobeline hydrochloride, dimorpholamine, naloxone hydrochloride, and the like); antimigraine agents (dihydroergotamine mesilate, sumatriptan, ergotamine tartrate, flunarizine hydrochloride, cyproheptadine hydrochloride, and the like); antihistamines (clemastine fumarate, diphenhydramine tannate, chlorpheniramine maleate, diphenylpyraline hydrochloride, promethazine, and the like); bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, and the like); cardiotonics (isoprenaline hydrochloride, dopamine hydrochloride, and the like); coronary vasodilators (diltiazem hydrochloride, verapamil hydrochloride, isosorbide dinitrate, nitroglycerin, nicorandil, and the like); telangiectasis agents (nicametate citrate, tolazoline hydrochloride, and the like); non-smoking adjuvants (nicotine and the like); circulatory system agents (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride, and the like); arrhythmic agents (propranolol hydrochloride, alprenolol hydrochloride, procainamide hydrochloride, mexiletine hydrochloride, nadolol, disopyramide, and the like), anti-malignant ulcer agents (cyclophosphamide, fluorouracil, tegafur, procarbazine hydrochloride, ranimustine, irinotecan hydrochloride, fluridine, and the like); antihyperlipemic agents (pravastatin, simvastatin, bezafibrate, probucol, and the like); blood sugar depressants (glibenclamide, chlorpropamide, tolbutamide, glymidine sodium, glybuzole, buformin hydrochloride, and the like); anti-peptic ulcer agents (proglumide, cetraxate hydrochloride, spizofurone, cimetidine, glycopyrronium bromide); choleretic drugs (ursodesoxycholic acid, osalmid, and the like); gastrointestinal motility enhancers (domperidone, cisapride, and the like); hepatic disease agents (tiopronin and the like); antiallergic agents (ketotifen fumarate, azelastine hydrochloride, and the like); antiviral agents (aciclovir and the like); anti-vertigo agents (betahistine mesilate, difenidol hydrochloride, and the like); antibiotics (cefaloridine, cefdinir, cefpodoxime proxetil, cefaclor, clarithromycin, erythromycin, methylerythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, and the like); anti-addiction agents (cyanamide and the like); anorectic agents (mazindol and the like); chemotherapeutic drugs (isoniazid, ethionamide, pyrazinamide, and the like); blood coagulation promoters (ticlopidine hydrochloride and warfarin potassium); anti-Alzheimer agents (physostigmine, donepezil hydrochloride, tacrine, arecoline, xanomeline, and the like); serotonin receptor antagonist antiemetics (ondansetron hydrochloride, granisetron hydrochloride, ramosetron hydrochloride, azasetron hydrochloride, and the like); gout suppressants (colchicine, probenecid, sulfinpyrazone, and the like); and narcotic painkillers (fentanyl citrate, morphine sulfate, morphine hydrochloride, codeine phosphate, cocaine hydrochloride, pethidine hydrochloride, and the like).

These drugs may be used singly, or two or more of them may be used in combination. Drugs in the form of both an inorganic salt and an organic salt are also included as a matter of course so long as they are pharmaceutically acceptable salts. Although it is basic to contain the drug in the coating liquid, the drug can be supplied separately later through a through hole provided in the substrate of the microneedles without being contained in the coating liquid. A content of the (A) drug in the coating liquid is 0.1 to 80% by weight, preferably 1 to 70% by weight, and particularly preferably 5 to 60% by weight.

The coating liquid may contain polymer compounds different from the above drugs. Examples of the polymer compounds include polyethylene oxide, polyhydroxymethyl cellulose, hydroxypropyl cellulose, polyhydroxypropyl methylcellulose, polymethyl cellulose, dextran, polyethylene glycol, polyvinyl alcohol, polyvinyl pyrrolidone, pullulan, carmellose sodium, chondroitin sulfate, hyaluronic acid, dextran, and gum arabic.

In addition thereto, to the coating liquid, propylene carbonate, crotamiton, 1-menthol, peppermint oil, limonene, diisopropyl adipate, or the like as a solution adjuvant or an absorption accelerator or methyl salicylate, glycol salicylate, 1-menthol, thymol, peppermint oil, vanillylamide nonylate, capsicums extract, or the like as an efficacy adjuvant may be added as needed.

Furthermore, to the coating liquid, a stabilizer, an antioxidant, an emulsifier, a surfactant, salts, or the like may be added as needed. Although the surfactant may be any of a nonionic surfactant and an ionic surfactant (cationic, anionic, or amphoteric), the nonionic surfactant normally used for pharmaceutical bases is preferable in terms of safety. More specific examples include sugar alcohol fatty acid esters such as sucrose fatty acid esters, sorbitan fatty acid esters, glycerin fatty acid esters, polyglycerin fatty acid esters, propylene glycol fatty acid esters, polyoxyethylene sorbitan fatty acid esters, polyoxyethylene glycerin fatty acid esters, polyethylene glycol fatty acid esters, polyoxyethylene castor oils, and polyoxyethylene hydrogenated castor oils.

Other known preparation auxiliary substances may be added to the coating liquid so long as they do not have any harmful effect on characteristics of solubility and viscosity required for the coating of the coating liquid and characteristics and properties of the dried coating layer.

The coating liquid requires a certain degree of viscosity so as not to cause dripping and specifically requires a viscosity of about 100 to 100,000 cps. A more preferable viscosity of the coating liquid is 100 to 60,000 cps, and the viscosity is within this range, whereby a desired amount of the coating liquid can be coated at one time without depending on the material of the microneedles 44. In general, a higher viscosity tends to increase an coated amount of the coating liquid, and when the viscosity is less than 600 cps, it is difficult to coat the microneedles 44 with a minimum amount of the coating liquid. However, unexpectedly, being 45,000 cps or more causes the drug content in the obtained coating layer 46 to turn to decrease. From this characteristic, if the viscosity of the coating liquid is a viscosity of 45,000 cps or more, enough content of the drug in the coating layer 46 corresponding to a used drug is not expected, which is economically unfavorable, and it is particularly preferable that the viscosity of the coating liquid be 600 to 45,000 cps.

EXAMPLES

Although the present invention will be specifically described based on examples below, the present invention is not limited to the following examples.

Example 1

A system for manufacturing a therapeutic microneedle including a compressor, a compressed air temperature regulator, an airflow rate regulator, an air filter, and a humidity regulator in this order was prepared. As the humidity regulator, a hollow fiber module and a constant-temperature water tank were used in combination. Specifically, the hollow fiber module was connected so that a gas flowing through the inside of the system would pass through the inside of a hollow fiber shaped membrane of the hollow fiber module and so that water at a constant temperature (24.5° C.) supplied from the constant-temperature water tank would be in contact with the outside of the hollow fiber shaped membrane of the hollow fiber module and circulate between the hollow fiber module and the constant-temperature water tank. For an air blowing line that connects the devices with each other, a Teflon (registered trademark) tube and a silicon tube were used, and a heat reserving material formed of a formed nitrile synthetic rubber as a heat insulating material was placed around the tubes. Details of the used devices are as follows:

Compressor: with a control pressure of 0.6 to 0.8 MPa and a discharge air amount of 85 L/min Compressed air temperature regulator: of the electronic cryogenic type with a set discharge temperature of 23° C.

Airflow rate regulator: with a set airflow rate of 30 L/min

Air filter: formed of polytetrafluoroethylene, with a pore size of 0.2 μm and an effective area of 50 $cm^2$ Constant-temperature water tank: a circulating constant-temperature water tank Hollow fiber module: a cylindrical module incorporating 230 hollow fibers formed of a fluorine ion exchange resin with an inner diameter of 1 mm, an outer diameter of 1.3 mm, and a length of 300 mm.

The prepared system for manufacturing a therapeutic microneedle was connected to a coating chamber via a polypropylene tube. As the coating chamber, an acrylic chamber was used. The coating chamber was further covered with a booth, and temperature and humidity within the booth were controlled using a precise temperature and humidity unit. The devices were started up, and the inside of the coating chamber was filled with air with temperature and humidity regulated.

Figure 7:
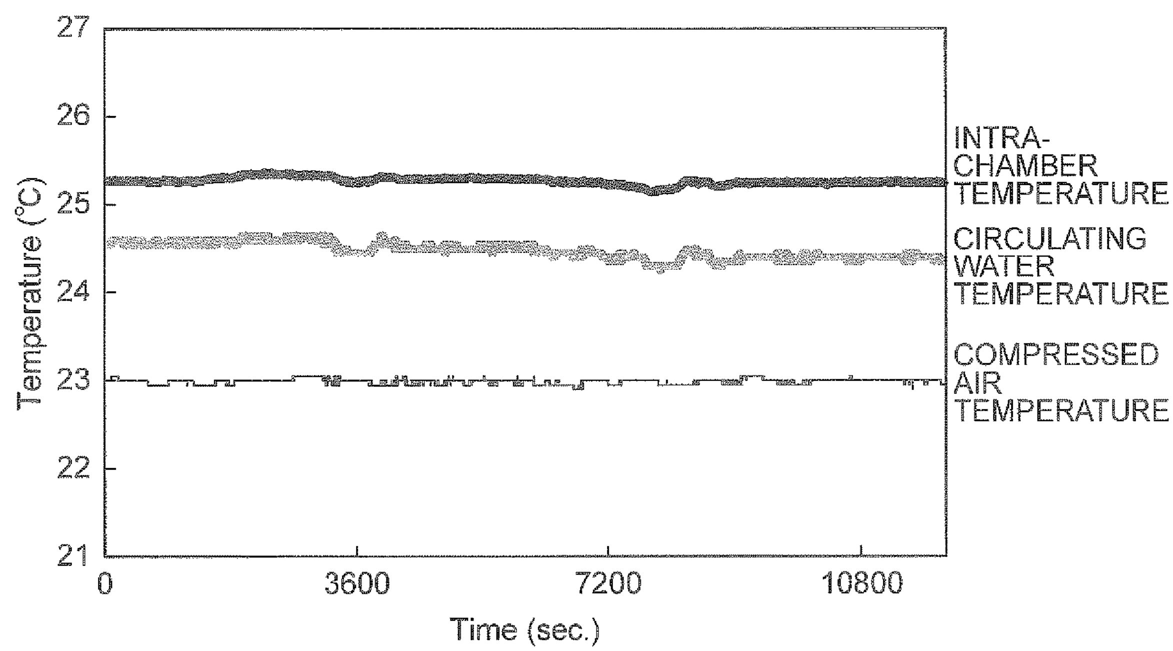
FIG. 7 (*a*) is graph illustrating a temperature progression within a coating chamber, and (b) is a graph illustrating a humidity progression within the coating chamber.
Figure 7:
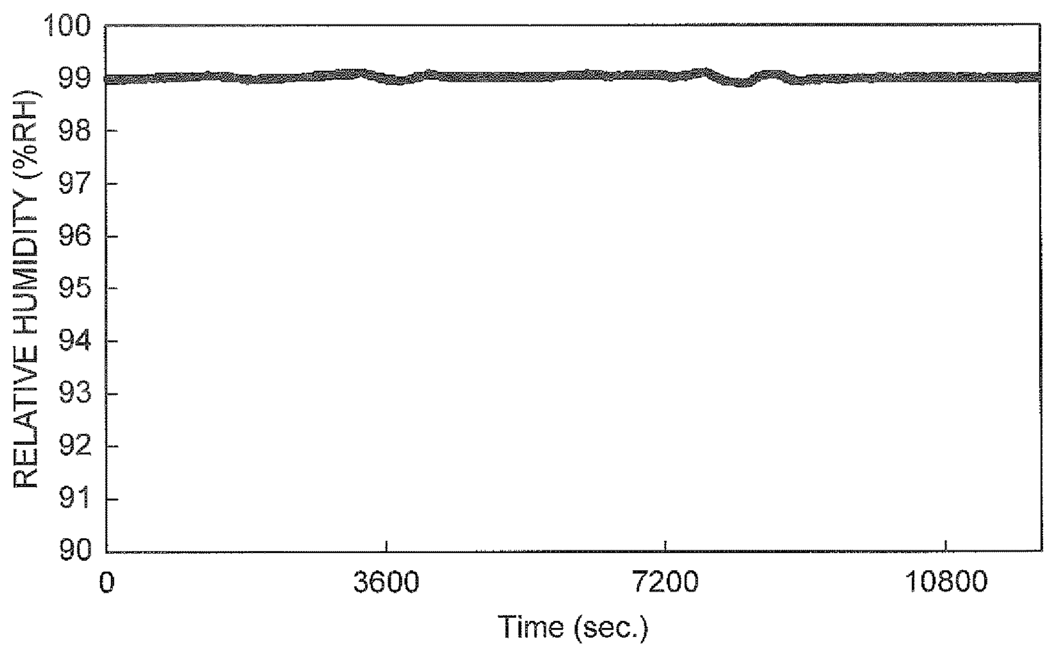

The temperature and humidity within the coating chamber were measured in time series. The results are illustrated in FIGS. 7 (*a*) and (*b*). By using the system of Example 1, the temperature and humidity within the coating chamber were able to arbitrarily be regulated.

Examples 2 and 3

Figure 8:
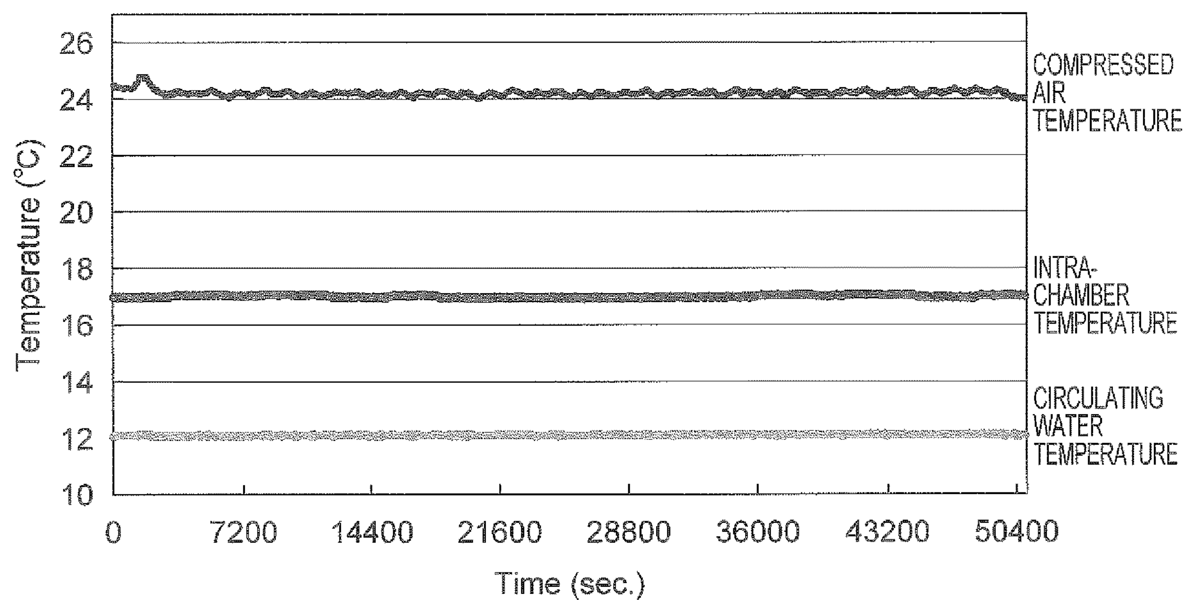
FIG. 8 (*a*) is a graph illustrating a temperature progression within the coating chamber, and (b) is a graph illustrating a humidity progression within the coating chamber.
Figure 8:
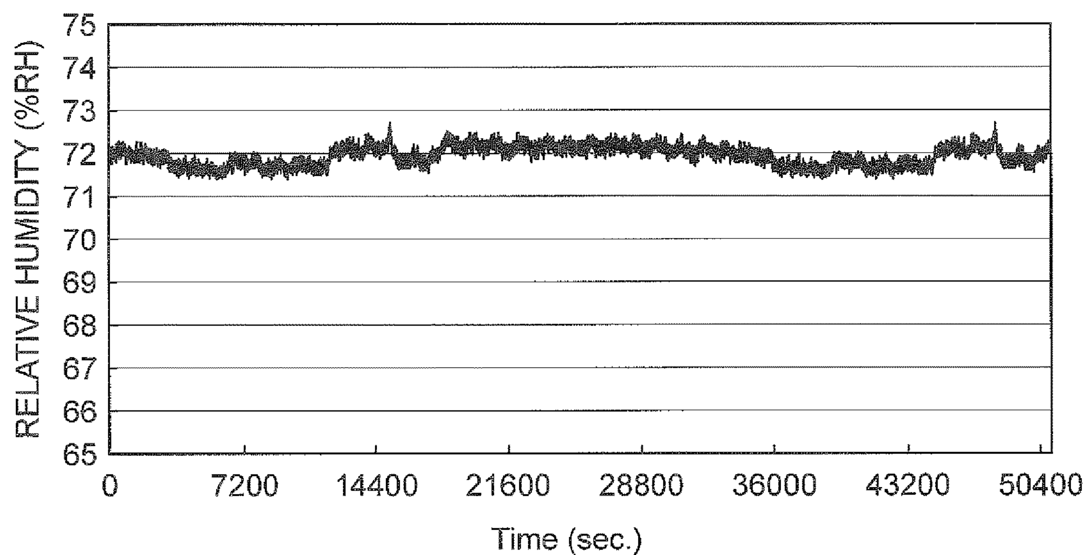
Figure 9:
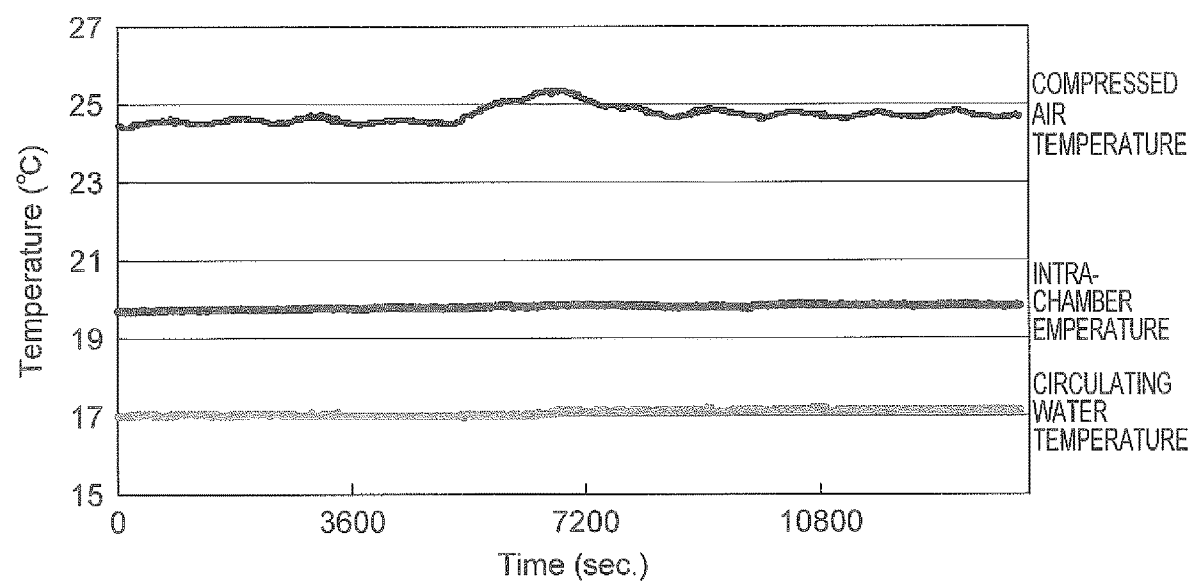
FIG. 9 (*a*) is a graph illustrating a temperature progression within the coating chamber, and (b) is a graph illustrating a humidity progression within the coating chamber.
Figure 9:
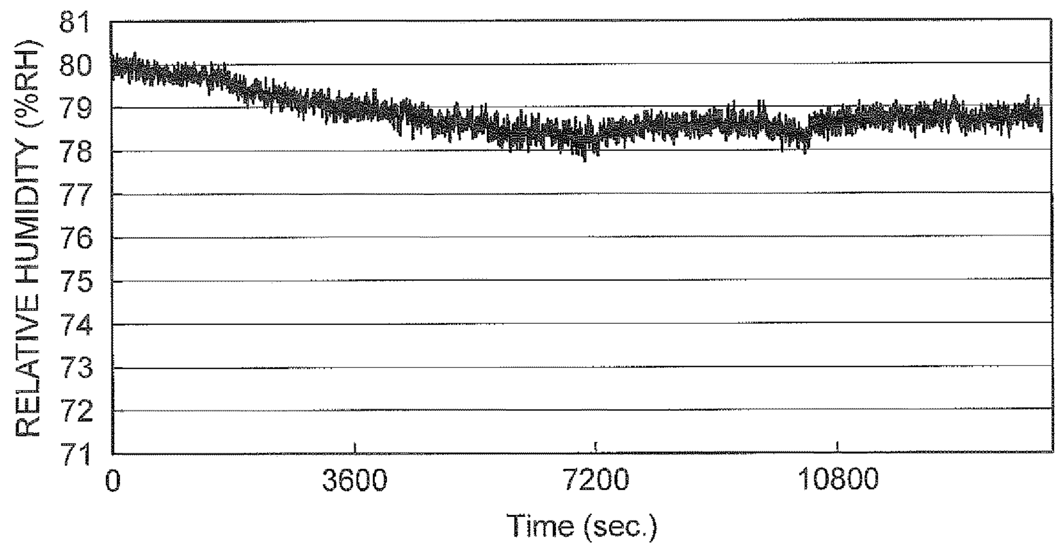

The inside of the coating chamber was filled with air with temperature and humidity regulated by the same method as Example 1 except that the temperature of the water supplied from the constant-temperature water tank to the outside of the hollow fiber shaped membrane of the hollow fiber module was changed to 12° C., and the temperature and humidity within the coating chamber were measured in time series (Example 2). The results are illustrated in FIGS. 8 (*a*) and (*b*). The inside of the coating chamber was filled with air with temperature and humidity regulated by the same method as Example 1 except that the temperature of the water supplied from the constant-temperature water tank to the outside of the hollow fiber shaped membrane of the hollow fiber module was changed to 17° C., and the temperature and humidity within the coating chamber were measured in time series (Example 3). The results are illustrated in FIGS. 9 (*a*) and (*b*). The inside of the coating chamber was able to be regulated to any humidity of 70% RH or more.

<Coating Test>

Within the coating chamber with the temperature and humidity regulated by the method of Example 1, a coating test on a microneedle device was carried out. A specific method of the coating test is as follows:

(Microneedle)

Material: polylactic acid; height: 500 μm; density: 625/cm$^2$; and a preparation area of the microneedle device: 1 cm$^2$/patch (Coating Liquid)

FR-40 (Food Red No. 40, a model drug) and pullulan were mixed with water so that their concentrations would be 1% by mass and 24% by mass, respectively, whereby a coating liquid was obtained.

Coating the microneedles with the coating solution was performed by the method illustrated in FIG. 6 (*a*) through (*c*). The obtained coating liquid was swept with a spatula on a metal mask plate (with a thickness of 100 μm, an aperture diameter of 250 μm, and a pitch of 400 μm) placed within the coating chamber and was filled into the apertures of the metal mask plate. By inserting the microneedles into the filled apertures and pulling them out thereof, the coating liquid coated the microneedles. The microneedles after the coating were air-dried and were stored at room temperature. The time required for the coating to 200 microneedles devices was about 2 hours.

Method of quantifying model drug: The drug on the microneedles after being air-dried was extracted with 1 ml of water. Absorbance at 504 nm of an extract obtained by the extraction was measured using an absorbance meter. From the obtained measurement value, an FR-40 content per one sheet of therapeutic microneedle was measured.

Figure 10:
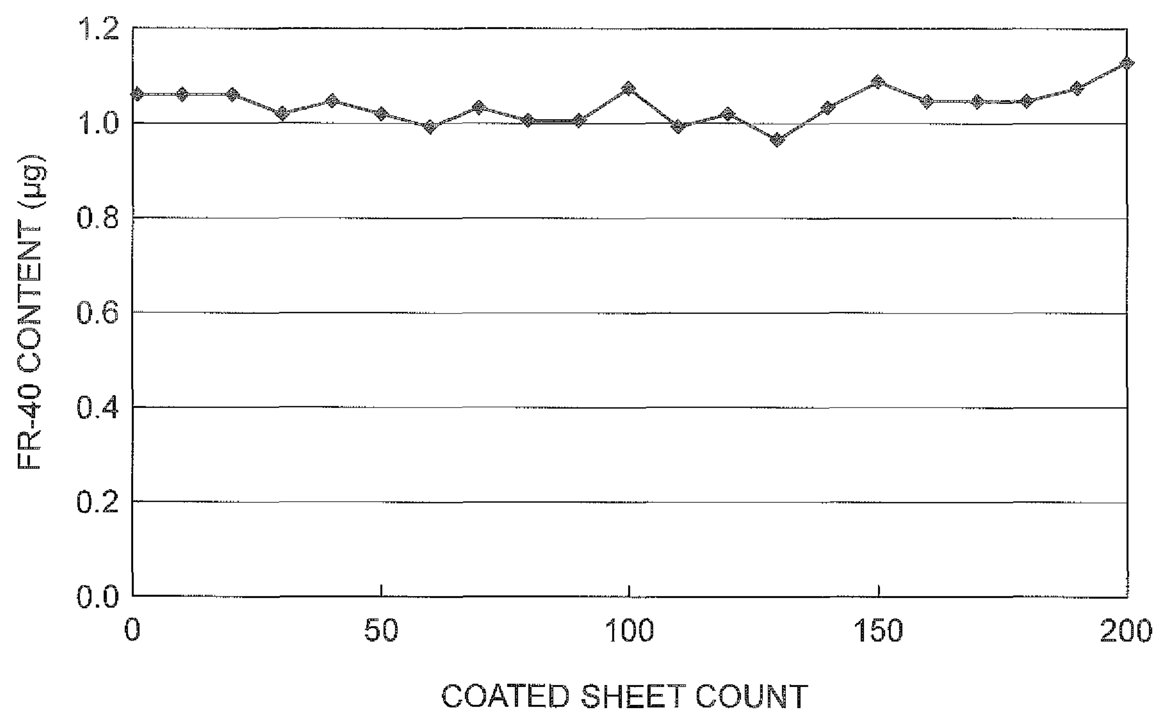
FIG. 10 is a graph illustrating a content of a drug coated on microneedles.

The measurement result of a model drug content after being dried is illustrated in FIG. 10. When a model formulation coating liquid was coated to the 200 microneedle devices, variations in the model drug content on the microneedles after being dried among the devices were extremely small; the average of the model drug content was 1.04 μg, the standard deviation was 0.04 μg, and the CV value was 3.58%.

Example 4

The following airflow rate regulation test was carried out using a system for manufacturing a therapeutic microneedle including a compressor, a compressed air temperature regulator, an airflow rate regulator, an air filter, and a humidity regulator in this order similarly to Example 1. The humidity within the coating chamber was set to 97% RH and 98% RH. In the respective humidities, the airflow rates listed in Table 1 were regulated by the airflow rate regulator, and coating tests were carried out in the respective conditions. The coating tests were carried out similarly to Example 1 except that the coating liquid, in which OVA and pullulan were mixed with water so that their concentrations would be 25% by mass and 15% by mass, respectively, was used. An OVA content on the microneedles after the coating liquid had been dried was measured. The results are listed in Table 1. By increasing the airflow rate, the OVA content on the microneedles after being dried increased. By controlling the airflow rate, the drug amount coating the microneedles was able to be regulated.

TABLE 1

| Humidity | Airflow rate | OVA content |
|---|---|---|
| 97% RH | 3.2 L/min | 56 μg |
| | 10 L/min | 75 μg |
| 98% RH | 22 L/min | 79 μg |
| | 30 L/min | 84 μg |

Example 5

Figure 11:
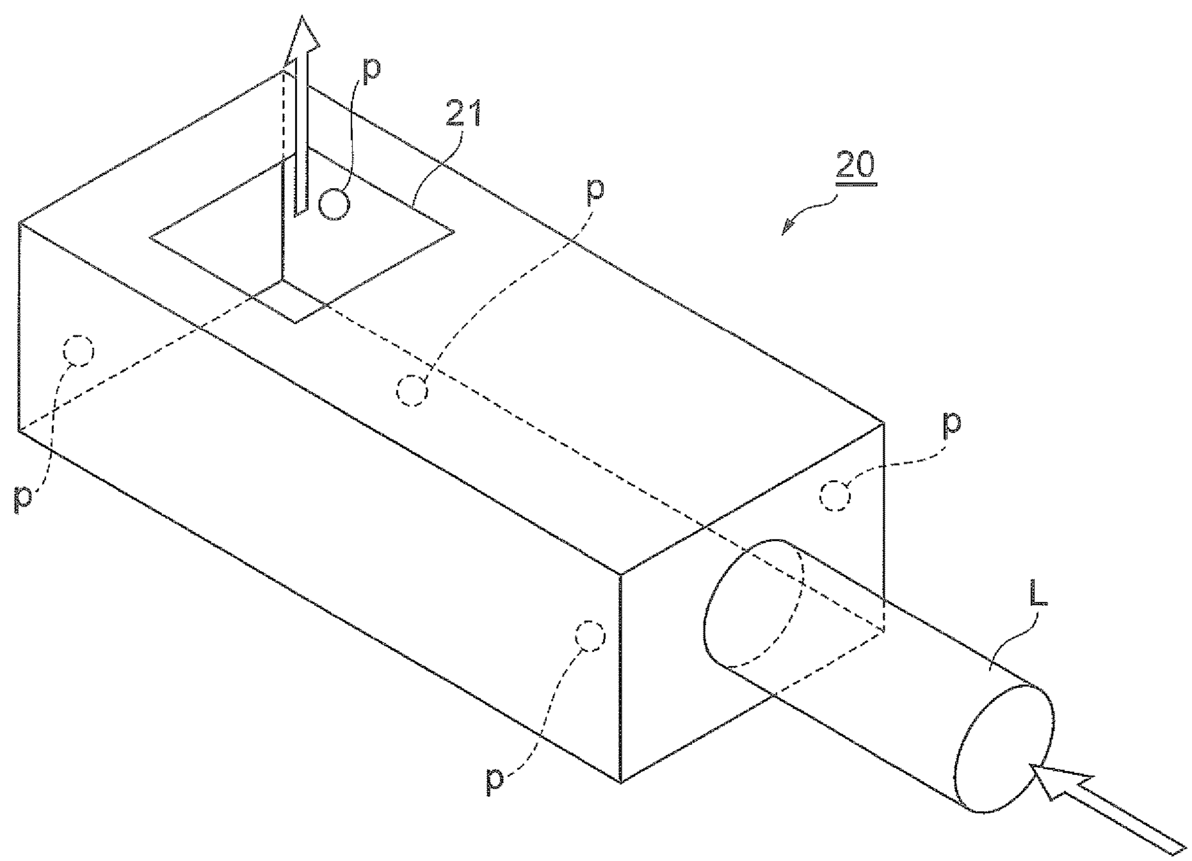
FIG. 11 is a schematic perspective view illustrating a coating chamber for an airflow rate regulation test.

Using a system similar to Example 1 and a coating chamber illustrated in FIG. 11, an airflow rate regulation test was carried out. The dimensions of the coating chamber are as follows:

Height: 35 mm; width: 50 mm; length: 205 mm; and volume: about 0.359 L

Discharge port (aperture) 21: a rectangle of 25 mm×30 mm

Air inlet to which the air blowing line L is connected: a circle with a diameter of 16 mm.

The devices of the system were started up, the airflow rate was set to the respective values listed in Table 2 by the airflow rate regulator, and a temperature of the constant-temperature water tank, a circulating water amount, and a temperature of the compressed air were appropriately regulated as needed. A total of five measurement positions p were provided at a center and four corners within the coating chamber, which were positioned at half the height of the coating chamber. Humidity was measured at each of the measurement positions p, and an average humidity of the five points, a standard deviation (SD), and a CV value were determined. The results are listed in Table 2. Even for any value of the airflow rate, the humidity was able to freely be regulated, and when the airflow rate was a certain amount or more, the humidity within the coating chamber was able to be regulated further uniformly.

TABLE 2

| | 5-point measurement (center + four corners) | | |
|---|---|---|---|
| Airflow rate (L/min) | Average humidity (% RH) | Standard deviation (% RH) | CV value (%) |
| 0.5 | 78.8 | 15.0 | 19.0 |
| 1.1 | 81.7 | 16.3 | 20.0 |
| 1.5 | 84.9 | 12.9 | 15.1 |
| 2.1 | 88.1 | 2.8 | 3.2 |
| 2.6 | 88.5 | 1.5 | 1.7 |
| 5.4 | 92.8 | 1.1 | 1.2 |
| 30 | 78.8 | 0.5 | 0.6 |

Comparative Example 1

Figure 12:
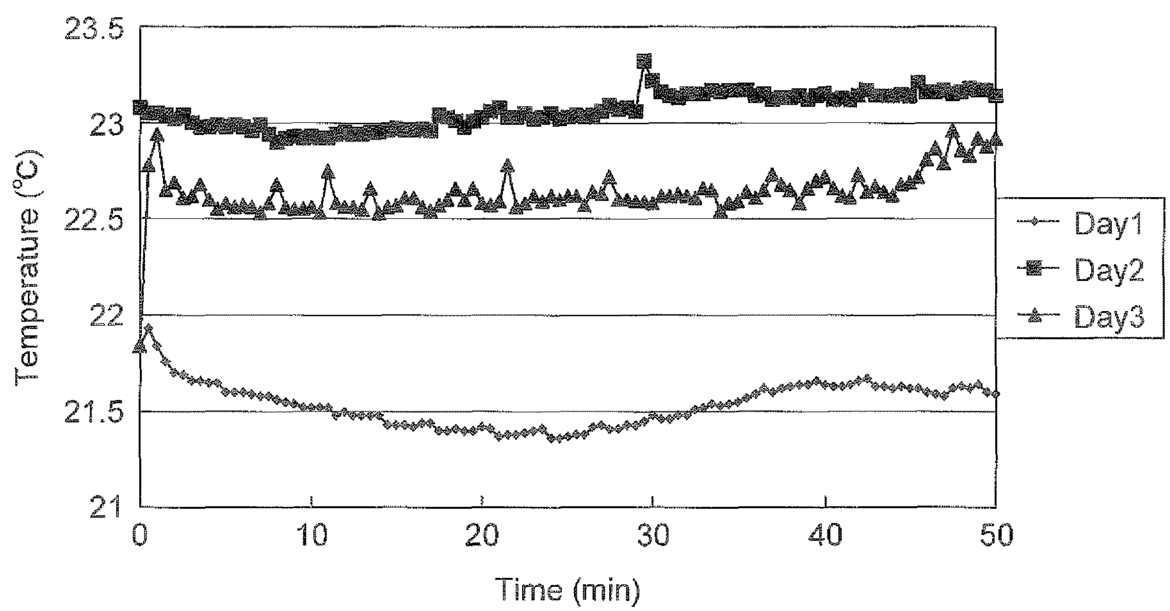
FIG. 12 (*a*) is a graph illustrating a temperature progression within the coating chamber, and (b) is a graph illustrating a humidity progression within the coating chamber.
Figure 12:
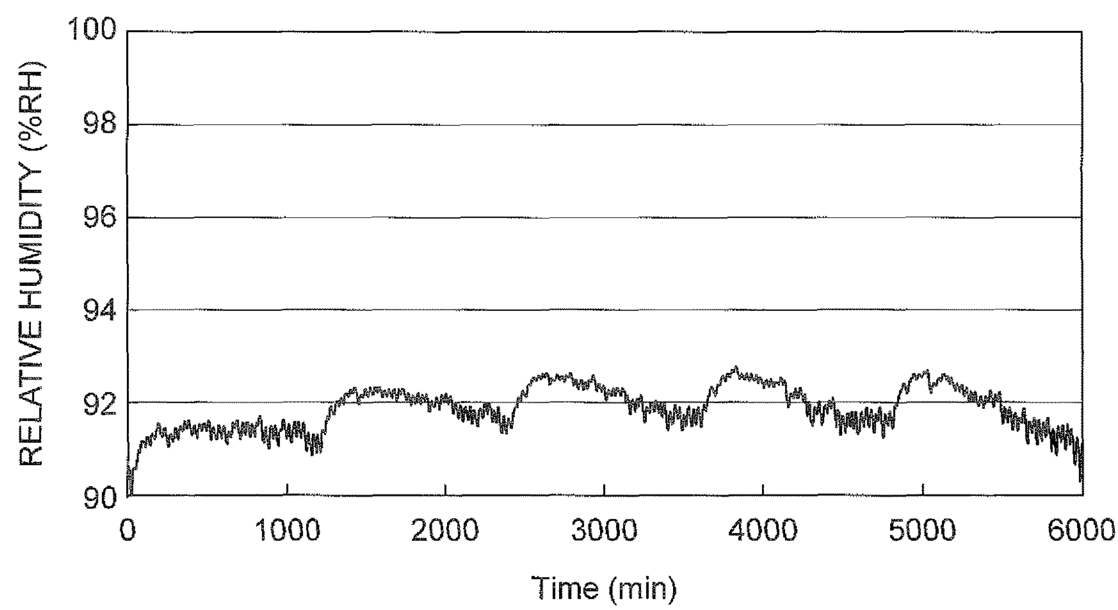
Figure 13:
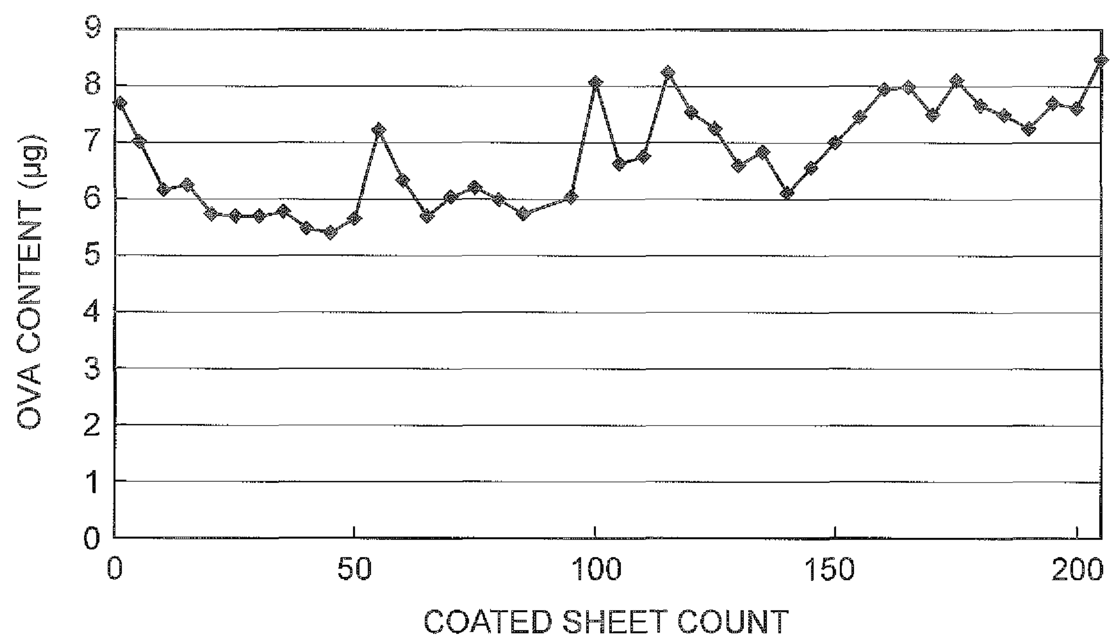
FIG. 13 is a graph illustrating a content of a drug coated on the microneedles.

A compressor, an airflow rate regulator, and a humidity regulator were connected with each other in this order via an air blowing line. For the compressor and the airflow rate regulator, the same ones as Example 1 were used, and setting was similarly performed. As the humidity regulator, only a circulating constant-temperature water tank was used. Progressions in temperature and relative humidity within the coating chamber were measured. The results are illustrated in FIGS. 12 (*a*) and (*b*). Inter-day and intra-day fluctuations in the temperature within the coating chamber were seen. The relative humidity within the coating chamber also considerably fluctuated. Within this coating chamber, a coating test on the microneedles was carried out similarly to Example 1 except that OVA was used as a model compound. A content of the model compound on the microneedles after the coating liquid had been dried was measured. The result is illustrated in FIG. 13. As a result of coating 200 sheets of microneedle devices with the coating solution, the content of the model compound considerably varied for each of the microneedle devices, and the CV value was 13.5%.

REFERENCE SIGNS LIST

10 Air compressor, 12 Compressed air temperature regulator, 14 Airflow rate regulator, 16 Air filter, 18 Humidity regulator, 20 Coating chamber, 21 Aperture, 22 Water supplier, 23 Water-vapor permeable membrane, 24 Water-vapor permeable membrane device, 26 Temperature and humidity sensor (temperature sensor and humidity sensor), 28 Controller (first to fourth control means), 30 Pressure regulator, 40 Therapeutic microneedle, 42 Substrate, 44 Microneedle, 46 Coating layer, 50 Coating liquid, 52 Mask plate, 54 Spatula, 56 Aperture, 100, 200 System for manufacturing therapeutic microneedle, L Air blowing line

The invention claimed is:

1. A system for manufacturing a therapeutic microneedle comprising:
   - a coating chamber for coating a microneedle with a coating liquid containing a drug;
   - an air compressor;
   - a humidity regulator configured to regulate humidity of air supplied from the air compressor to an inside of the coating chamber to 70% (RH) or more;
   - an air filter configured to eliminate microorganisms from air to be supplied to the inside of the coating chamber;
   - an airflow regulator;
   - an air blowing line connected to the coating chamber, wherein the air blowing line is configured to supply only the air with the regulated humidity into the coating chamber; and
   - means for discharging pre-existing air from the coating chamber, the air with the regulated humidity replacing the pre-existing air,
   - wherein the humidity regulator is a water-vapor permeable membrane humidity regulator in which the air supplied from the air compressor and water as a humidity regulation source are separated from each other by a water-vapor permeable membrane and is configured to regulate humidity by regulating temperature of the water.

2. The system for manufacturing a therapeutic microneedle according to claim 1, further comprising a compressed air temperature regulator configured to regulate temperature of the air supplied from the air compressor.

3. The system for manufacturing a therapeutic microneedle according to claim 2, further comprising: a humidity sensor; and a first controller for controlling the compressed air temperature regulator based on a signal corresponding to a humidity detected by the humidity sensor.

4. The system for manufacturing a therapeutic microneedle according to claim 2, further comprising: a temperature sensor; and a second controller for controlling the compressed air temperature regulator based on a signal corresponding to a temperature detected by the temperature sensor.

5. The system for manufacturing a therapeutic microneedle according to claim 1, wherein the water-vapor permeable membrane is formed into a hollow fiber shape.

6. The system for manufacturing a therapeutic microneedle according to claim 1, wherein the humidity regulator includes a water supplier configured to supply water.

7. The system for manufacturing a therapeutic microneedle according to claim 6, wherein the water supplier is a constant-temperature water tank.

8. The system for manufacturing a therapeutic microneedle according to claim 6, wherein the water supplier is capable of regulating water temperature.

9. The system for manufacturing a therapeutic microneedle according to claim 8, further comprising: a humidity sensor; and a third controller for controlling water temperature of the water supplier based on a signal corresponding to a humidity detected by the humidity sensor.

10. The system for manufacturing a therapeutic microneedle according to claim 8, further comprising: a temperature sensor; and a fourth controller for controlling the water temperature of the water supplier based on a signal corresponding to a temperature detected by the temperature sensor.

11. A method of manufacturing a therapeutic microneedle comprising:
   - a step of regulating humidity of air to be fed to a coating chamber to 70% (RH) or more by a humidity regulator;
   - a step of eliminating microorganisms from the air by an air filter;
   - a step of introducing humidity-regulated, microorganism-eliminated air into the coating chamber wherein the humidity of air has regulated to 70% (RH) or more;
   - a step of coating a microneedle with a coating liquid containing a drug in the coating chamber wherein the humidity-regulated, microorganism-eliminated air has been introduced into the coating chamber; and an airflow regulator, wherein the humidity regulator is a water-vapor permeable membrane humidity regulator in which the air supplied from the air compressor and water as a humidity regulation source are separated from each other by a water-vapor permeable membrane and is configured to regulate humidity by regulating temperature of the water, and wherein pre-existing air is discharged from the coating chamber, the humidity-regulated, microorganism-eliminated air replacing the pre-existing air.

* * * * *